United States Patent [19]

Vrignaud

[11] Patent Number: 5,758,380
[45] Date of Patent: Jun. 2, 1998

[54] DEVICE FOR COMPREHENSIVE ORAL HYGIENE

[75] Inventor: Jean Louis Vrignaud, Scottsdale, Ariz.

[73] Assignee: Devmark Ltd., Luxembourg, Luxembourg

[21] Appl. No.: 821,113

[22] Filed: Mar. 20, 1997

Related U.S. Application Data

[63] Continuation of Ser. No. 56,174, Jun. 25, 1996, Pat. No. Des. 386,315, Ser. No. 62,132, Nov. 7, 1996, Ser. No. 62,133, Nov. 7, 1996, Ser. No. 62,134, Nov. 7, 1996, Ser. No. 62,367, Nov. 7, 1996, and Ser. No. 62,368, Nov. 7, 1996.

[51] Int. Cl.⁶ .................................................. A46B 9/04
[52] U.S. Cl. ............................ 15/106; 15/111; 15/167.2
[58] Field of Search ...................... 15/106, 111, 167.1, 15/167.2; D4/105, 106, 119, 120, 138

[56] References Cited

U.S. PATENT DOCUMENTS

| 2,229,664 | 1/1941 | Meeske | 15/106 |
|---|---|---|---|
| 2,528,992 | 11/1950 | Barr | 15/167.2 |
| 5,226,197 | 7/1993 | Nack et al. | 15/111 |
| 5,305,491 | 4/1994 | Hegemann | 15/167.2 |
| 5,327,607 | 7/1994 | Wagner | 15/167.2 |
| 5,497,526 | 3/1996 | Klinkhammer | 15/167.2 |

FOREIGN PATENT DOCUMENTS

| 4115943 | 11/1991 | Germany | 15/167.2 |

*Primary Examiner*—David Scherbel
*Assistant Examiner*—Terrence R. Till
*Attorney, Agent, or Firm*—Richard R. Mybeck; Peter B. Scull

[57] ABSTRACT

An oral hygiene device having, in one embodiment, a unique, unrestricted, self-adjusting two-headed gum-specific brush on one end of a handle; and in another embodiment, a two-headed gumbrush on one end of an elongated handle and a toothbrush on the opposite end of the handle. A tongue scraper may also be included on the toothbrush end of the device.

13 Claims, 3 Drawing Sheets

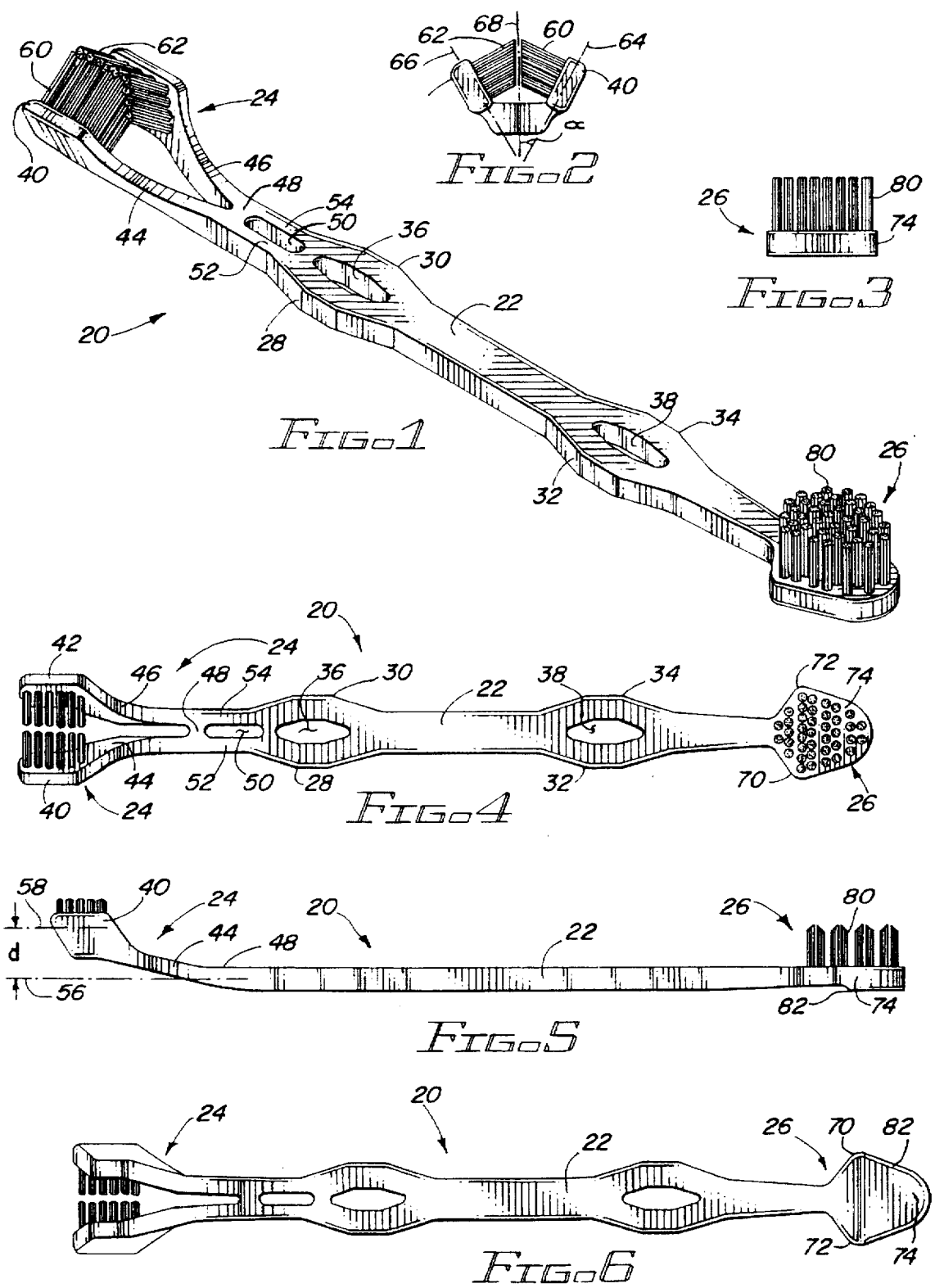

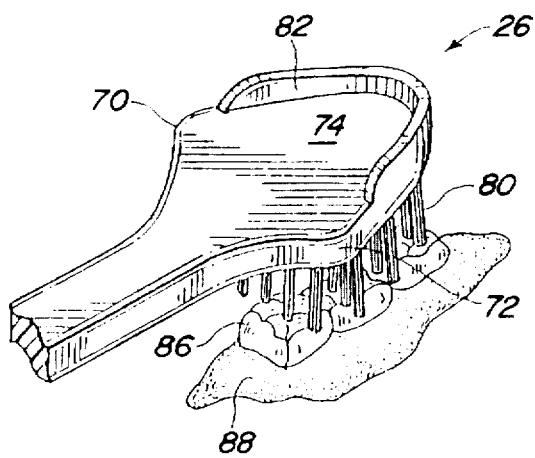
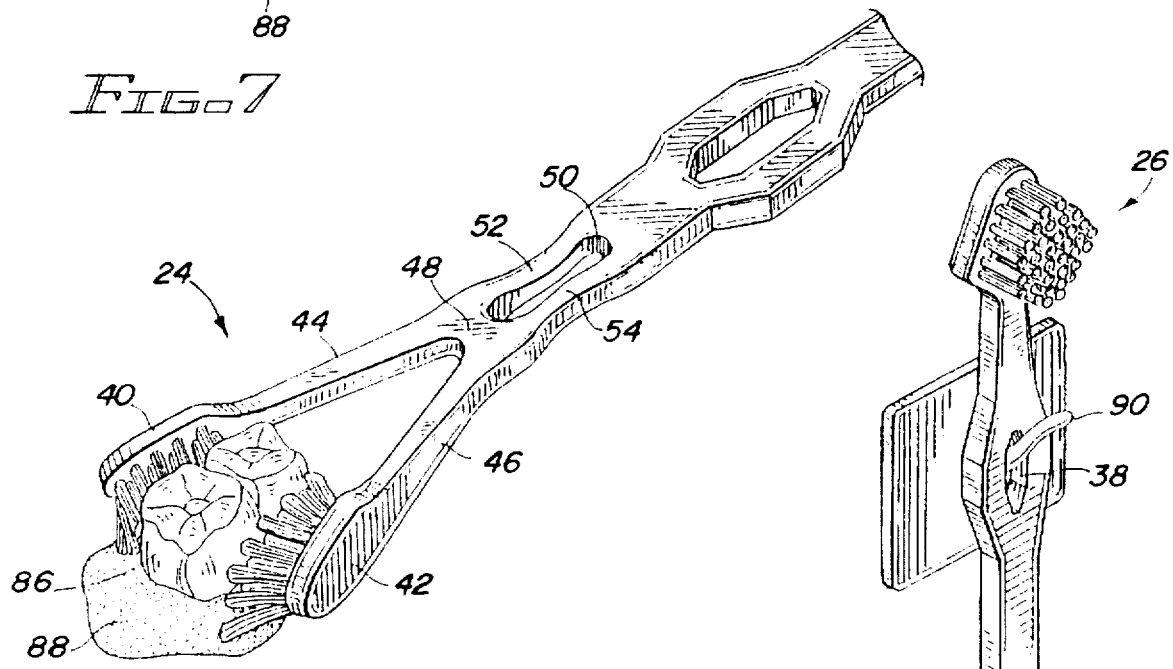
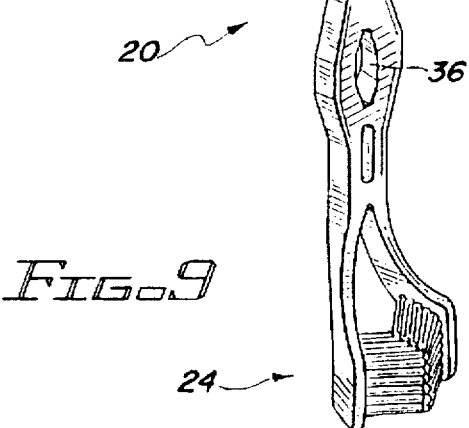

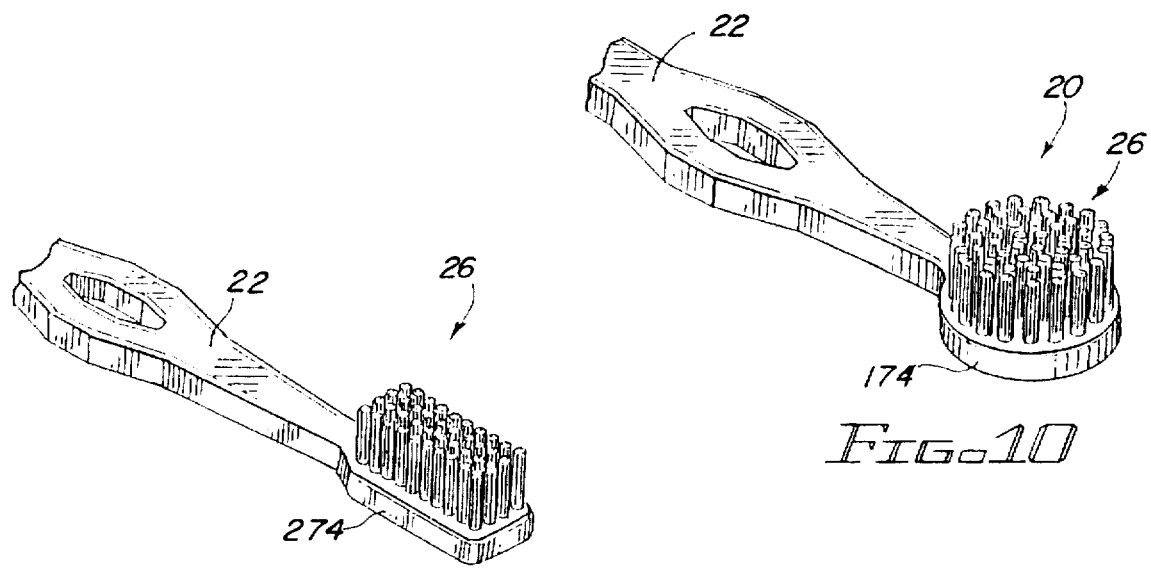
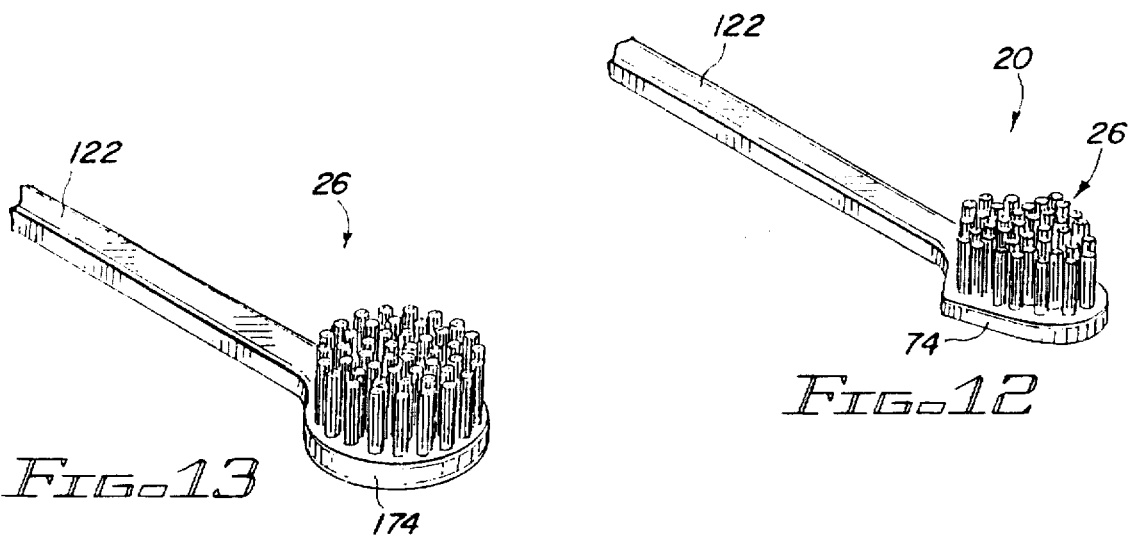
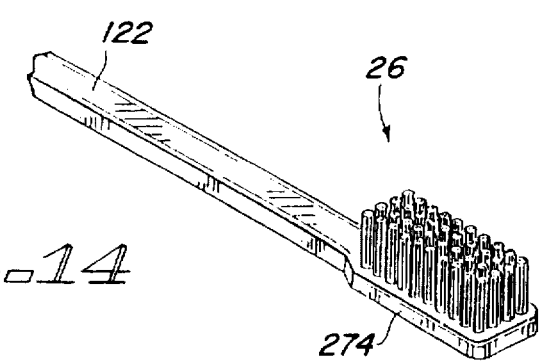

DEVICE FOR COMPREHENSIVE ORAL HYGIENE

This application is a continuation of my Design Pat. Application No. 29/056,174, filed Jun. 25, 1996, now Pat. D 386,315 and of my Design Pat. Applications Nos. 29/062, 132; 29/062,133; 29/062,134; 29/062,367; and 29/062,368, all filed Nov. 7, 1996.

INTRODUCTION

The present invention is directed generally to oral hygiene devices and more particularly to a device having a unique two-headed gumbrush with or without a toothbrush on the other end of the handle. A tongue scraper may also be incorporated into the device.

BACKGROUND OF THE INVENTION

The art of oral hygiene devices is replete with multi-headed brush elements. For example, the concept of opposing arms disposed on the same end of a handle in which brushes on each arm are disposed in generally opposing relationship to each other is shown in Ruff (U.S. Pat. No. 1,679,946), Davis (U.S. Pat. No. 1,908,509), Dinhofer (U.S. Pat. No. 2,807,820), Froidevaux (U.S. Pat. No. 3,953,907 ), Weiss (U.S. Pat. No. 4,498,209), Klinkhammer (U.S. Pat. No. 5,316,027) and UK Patent Application GB 2192784 A. Flexible arms are also shown in several of these patents.

Further, numerous double-ended oral hygiene devices have also been disclosed in the prior art. For example, toothbrushes disposed on both ends of a handle have been shown in Hartman (U.S. Pat. No. 1,360,292), Wickberg (U.S. Pat. No. 1,469,348), Hachman (U.S. Pat. No. 2,095,741), Kohler et al. (U.S. Pat. No. 2,139,593), Pandiyan (U.S. Pat. No. 2,251,853), Hyman (U.S. Pat. No. 3,754,295), Wiley (U.S. Pat. No. 4,053,959) and Chan (U.S. Pat. No. 5,522,109) among others. Moreover, most of these involve a fairly conventional toothbrush on one end of the handle, and a more specialized brush on the other. The more specialized brushes include those which are intended to clean the interior surfaces of teeth (Hartman, Wickberg and Wiley), as well as those for cleaning the occlusal, labial, buccal and lingual surfaces (Kolher et al. and Chan) and the sulcular area (Hyman). Other functional reasons for such double-ended arrangements are also disclosed (Hachman).

Moreover, the structural disposition of oral cleaning devices of a plurality of types (including brushes and non-brush devices) on both ends of a handle have been shown. See, for example, Brothers et al. (U.S. Pat. No. 2,083,217), Kohler et al., Greenacre (U.S. Pat. No. 3,672,377), Snider (U.S. Pat No. 4,488,327), Hitzman (U.S. Pat. No. 4,724,570) and Yen-Hui (U.S. Pat. No. 5,005,246). Of these, tongue scrapers are shown in Brothers et al, Snider and Yen-Hui. Fixed ridge-type tongue scrapers are shown in Brothers et al.

However, none of the references either teach or suggest a device having an unobstructed gumbrush disposed on one end of a handle and a toothbrush disposed on the other end of the handle to provide a comprehensive oral hygiene device. Moreover, the art of opposing arm brushes has not satisfactorily addressed the need for greater flexibility and/or unobstructed maneuverability for gum cleaning and massaging.

BRIEF SUMMARY OF THE INVENTION

The present invention is directed primarily to a comprehensive oral hygiene device having a unique gumbrush disposed at one end of an elongated handle and, when desired, a toothbrush at the other end of the handle. The gumbrush of the present invention has two heads which are disposed in angular, generally opposing coactive relationship to each other. Each of the two heads is attached to a separate flexible arm and each arm being directly attached to the elongated handle. The flexibility of the gumbrush arms may be enhanced by a pivot point and a slot which provides reduced resistance in the handle to the outward flexure of the arms. This two-headed gumbrush arrangement provides for unobstructed movement of the gumbrush down onto the gum tissue unlike the many triple-headed or relatively inflexible gumbrushes of the prior art. In a preferred embodiment, the gumbrush heads and the flexible arms will be integrally formed with the elongated handle to reduce debris collection areas and thereby avoid bacterial growth and odor.

In another embodiment of the present invention, the gumbrush heads are formed on the proximal end of the elongated handle and a toothbrush is formed on its distal end to provide a more comprehensive oral hygiene device. Thus, a device for brushing the inner and outer gums and the sides of the teeth is disclosed herein which also provides the capability of brushing the chewing surfaces of the teeth as well as the palate and/or the tongue. Moreover, a tongue scraper is also disclosed which may be disposed on the toothbrush or distal end of the device of the present invention. The elongated handle may further be provided with one or more slots defined therein for, inter alia, providing means for simple storage of the device. Still further, the elongated handle may be provided with selected distended lateral surfaces which enhance grip, manipulation and control of the device when in use.

Accordingly, an object of the present invention is to provide a unique device which enables a user to attain comprehensive oral hygiene and includes a unique, flexible and unobstructed gumbrush.

Another object is to provide a device for comprehensive oral hygiene which includes an unobstructed gumbrush in combination with a tongue scraper and/or a toothbrush.

Yet another object is to provide a device for oral hygiene which has a unique handle for increased storage facility and provides improved manipulation, grip and control when in use.

These and still further objects as shall hereinafter appear are readily fulfilled by the present invention in a remarkably unexpected manner as will be readily discerned from the following detailed description of an exemplary embodiment thereof especially when read in conjunction with the accompanying drawings in which like parts bear like numerals throughout the several views.

BRIEF DESCRIPTION OF THE DRAWINGS

In the drawings:

FIG. 1 is an isometric view of an oral hygiene device embodying the present invention;

FIG. 2 is a proximal end elevation of the oral hygiene device of FIG. 1;

FIG. 3 is a distal end elevation of the oral hygiene device of FIG. 1;

FIG. 4 is a top plan view of the oral hygiene device of FIG. 1;

FIG. 5 is a side elevation of the oral hygiene device of FIG. 1;

FIG. 6 is a bottom plan view of the oral hygiene device of FIG. 1;

FIG. 7 is a fragmented isometric view of a toothbrush and tongue scraper of the present invention;

FIG. 8 is a fragmented isometric view of a gumbrush of the present invention;

FIG. 9 is an isometric view of an oral hygiene device and coactive hook in accordance with the present invention;

FIG. 10 is a fragmented isometric view of an alternative toothbrush for use with the present invention;

FIG. 11 is a fragmented isometric view of still another alternative toothbrush for use with the present invention;

FIG. 12 is an isometric view of yet another alternative embodiment of the present invention;

FIG. 13 is an isometric view of still another alternative embodiment of the present invention; and FIG. 14 is an isometric view of still one further alternative embodiment of the present invention.

DESCRIPTION OF THE PREFERRED EMBODIMENT

The present invention is particularly directed to a plurality of elements which when considered as an ensemble, provide comprehensive attainment and maintenance of oral cleanliness. Of these, there are three primary features; namely, an unobstructed gumbrush, a uniquely-shaped toothbrush and a tongue scraper.

Referring now to the drawings, an exemplary oral hygiene device of the present invention is shown in FIGS. 1–6 and is identified by the general reference numeral 20. As shown more particularly in FIGS. 1 and 4–6, device 20 generally includes an elongated handle 22, a gumbrush 24 and a toothbrush 26. In this embodiment, gumbrush 24 is disposed at one end of handle 22 and toothbrush 26 is disposed at the other, distal end of handle 22.

In the preferred embodiment shown in FIGS. 1–6, handle 22 is shown having lateral protrusions 28, 30 and 32, 34. Protrusions 28, 30 are defined as a pair of opposing protrusions, as is the respective pair of protrusions 32, 34. Each pair is near a respective end of handle 22. Defined between opposing protrusions 28,30 is an opening 36 which extends through handle 22. A similar opening 38 is defined between opposing protrusions 32, 34 and also extends through handle 22.

Gumbrush 24 comprises multiple features. Principal among these are heads 40 and 42 which are disposed in angled, generally opposed relationship to each other as will be further described below. Head 40 is integrally connected to a flexible arm 44 which in turn is integrally connected to handle 22. Likewise, head 42 is integrally connected to a flexible arm 46 which is also integrally connected to handle 22. A solid portion 48 of handle 22 is disposed at and connected to and between respective arms 44, 46 at their points of connection to handle 22. An elongated slot 50 may, as shown, be defined in handle 22 between flexible side walls 52, 54. Such a slot 50 is bordered at one end by solid portion 48 and accomplishes a purpose to be further described below.

Heads 40, 42 of gumbrush 24 are preferably offset or displaced, as shown in FIG. 5, a preselected distance "d" away from or off centerline 56 of handle 22. Distance "d" is measured between centerline 56 of handle 22 and centerline 58 of heads 40, 42 as shown in FIG. 5. This offset provides a benefit in reducing tooth obstruction when heads 40, 42 are moved to gum brushing depth as will be further described below.

Heads 40,42 of gumbrush 24 are, as mentioned above, disposed in angled, generally opposed relationship to each other. This means they are angled so that they define an angle α which is measured between the intersection of the extensions of centerlines 64 and 66, which as shown in FIG. 2 are defined through the respective centers of heads 40 and 42. Angle α is preferably between 46 and 66 degrees.

Each head 40, 42 of gumbrush 24 has a respective set 60, 62 of bristles disposed therein and emanating therefrom. As can be seen particularly in FIG. 2, bristles 60 extend generally perpendicularly out from head 40 relative to center line 64. Bristles 62 similarly extend generally perpendicularly out from head 42 relative to center line 66. Bristles 60 and 62 are generally clumped and embedded in heads 40, 42 as is generally known in the art. FIG. 2 also shows the graduated lengths of bristles 60 and 62. In FIG. 2, the lower bristles of each set 60, 62 are shorter than the upper bristles such that they generally define a meeting plane, represented by line 68 and extending perpendicular to the drawing page, at which the outer ends of bristles 60 meet or nearly meet the ends of bristles 62. Line 68 preferably splits angle α equally as shown.

In one embodiment of the present invention, gumbrush 24 is the sole brush disposed on a handle 22. However, as is also shown in FIGS. 1–6, the preferred embodiment of the present invention also has a toothbrush 26 disposed on handle 22. Toothbrush 26 is preferably disposed at the distal end of handle 22 opposite gumbrush 24.

A preferred toothbrush 26 according to the present invention is shown having first and second lateral bulges 70, 72. Bulges 70, 72 provide a wider head 74 for toothbrush 26 than usual. This provides a wider swath which is particularly useful when toothbrush 26 is also used to brush the palate or tongue.

Toothbrush 26 also has bristles 80 which, as are shown in FIGS. 1 and 3, may be flat, or, as shown in FIG. 5 have alternately angularly extending ends to provide better access to the corners (between the chewing surfaces and the sides) and/or depressions in the chewing surfaces of the teeth.

A tongue scraper 82 is also shown in the preferred embodiment, particularly in FIGS. 5, 6 and 7. Primarily, scraper 82 comprises a raised ridge which follows the outer contour of head 74 generally running from first bulge 70 to second bulge 72. The outer contour means that portion of the circumference of head 74 which is not immediately adjacent to handle 22.

The manufacture of the present invention generally follows the methods and procedures which are well known by those skilled in the art of toothbrush manufacture. The major distinctions reside instead in the shapes and dispositions of the structural elements. Further, the materials are also generally as are known in the art. Thus, the preferred embodiment of device 20 (including all brush heads, arms, etc.) will be molded as a single, integral piece of sturdy, yet flexible plastic into which soft nylon bristles 60, 62 and 80 will be embedded.

In use, toothbrush 26 particularly provides for the cleaning of the tops and sides of the crowns of a user's teeth in the usual way as shown in FIG. 7. If angularly extending bristles are used in brush 26, such as those shown in FIG. 5, then head 74 may be rotated slightly to provide better brushing access to the indentations on the chewing surfaces of the teeth or to allow simultaneous brushing of the chewing surfaces as well as the corners and upper sides of the teeth.

Toothbrush 26 is also useful for brushing the tongue and palate. The wider head 74 provides a wide area of contact that is particularly beneficial here. Plaque on the tongue and palate is at least loosened and may be removed by back and forth strokes of bristles 80.

Brush head 74 may then be flipped over and tongue scraper 82 can be pulled across the tongue and/or palate to scrape away the plaque. The scraper shown in the preferred embodiment is particularly useful for scraping along the length of the tongue preferably when pulled along the tongue from inside, deep in the mouth out to the tip of the tongue.

Device 20 may then be flipped end for end so that gumbrush 24 may be used to clean the lower sides of the teeth, the sulcular area between the teeth and gums as well as to clean and massage the gums. A typical user's teeth and gums are represented generally by teeth 86 and gums 88 in FIG. 8. The present two-headed, angled and opposing arrangement of heads 40, 42 of gumbrush 24 provides for an extended reach down onto the gums 88 as shown in FIG. 8. A still further unobstructed downward reach is provided by the offset distance "d" of heads 40, 42 from centerline 56 of handle 22. This provides a reach which is unhindered by any teeth physically abutting against or interfering with handle 22. Thus, heads 40, 42 will easily reach as far down onto the gums as needed to thoroughly clean and massage the entire gums. The flexible, yet shape-retaining arms 44, 46 provide for a continuous amount of pressure of bristles 60, 62 on the teeth and gums regardless the thickness of the teeth and/or gums being cleaned or massaged. Moreover, as shown in FIG. 8, slot 50 allows for inward flexure or bending of side walls 52 and 54 when arms 44, 46 are flexed outwardly. The inward flexure is caused partially by the transfer of bending forces from arms 44, 46 about the fulcrum of solid portion 48 to side walls 52, 54. Thus, solid portion 48 acts as a fulcrum or pivot point to reduce stress at the connection of gumbrush 24 to handle 22.

Still further, after oral cleaning (as described above) has been performed, device 20 may be simply stored in a hanging position as shown in FIG. 9. Device 20 may be hung on a simple hook 90 by engaging hook 90 with either opening 36 or 38.

Alternative shapes for many of the above described elements may also be used within the present invention. As shown in FIGS. 10 and 11, more conventional circular or rectangular heads 174 and 274 may be substituted for head 74 of brush 26 of the preferred embodiment. Also, as shown in FIG. 12, an elongated handle 122 having no lateral protrusions or slots may also be substituted for handle 22. Again, circular or rectangular heads 174 and 274 may be substituted for head 74 of brush 26 with a handle 122 as shown in FIGS. 13 and 14. In like manner, myriad other structural substitutions may also be used within the spirit of this invention.

From the foregoing, it is readily apparent that a new and useful embodiment of the present invention has been herein described and illustrated which fulfills all of the aforestated objects in a remarkably unexpected fashion. It is, of course, understood that such modifications, alterations and adaptations as may readily occur to the artisan confronted with this disclosure are intended within the spirit of this disclosure which is limited only by the scope of the claims appended hereto.

Accordingly, what is claimed is:

1. A device for oral hygiene comprising:

an elongated handle having first and second ends and in which said elongated handle has first and second sidewalls which define a slot therein between said first and second side walls of said handle whereby said slot is disposed adjacent said first end of said handle, and whereby said slot allows for inward flexure of said first and second side walls;

a gumbrush connected to said first end of said elongated handle, said gumbrush having first and second gumbrush heads, first and second flexible arms and first and second sets of bristles, each of said gumbrush heads having a respective one of said first and second sets of bristles disposed thereon;

whereby said first gumbrush head is attached to said first flexible arm, said first flexible arm being connected to said first end of said elongated handle, said second gumbrush head being attached to said second flexible arm, and said second flexible arm also being connected to said first end of said elongated handle; and whereby said first and second flexible arms are connected to said first end of said elongated handle so that first and second heads are disposed in angled, generally opposing relationship to each other.

2. A device according to claim 1, in which said elongated handle is integrally formed with said first and second flexible arms.

3. A device according to claim 1, in which each of said first and second gumbrush heads is disposed a discrete angle relative to each other.

4. A device according to claim 1, in which said elongated handle further comprises first and second lateral protrusions.

5. A device according to claim 1, in which said elongated handle has an opening defined therein; whereby said opening is adapted to receive a hook therein to suspend said device from said hook.

6. A device for oral hygiene comprising:

an elongated handle having first and second ends;

a gumbrush connected to said first end of said elongated handle, said gumbrush having first and second gumbrush heads, first and second flexible arms and first and second sets of bristles, each of said gumbrush heads having a respective one of said first and second sets of bristles disposed thereon; said first gumbrush head being attached to a first flexible arm, said first flexible arm being connected to said first end of said elongated handle, said second gumbrush head being attached to a second flexible arm, and said second flexible arm also being connected to said first end of said elongated handle;

whereby said first and second flexible arms are connected to said first end of said elongated handle so that said first and second heads are disposed in angled, generally opposing relationship to each other;

a toothbrush connected to said second end of said elongated handle, whereby said toothbrush is adapted to brush the crowns of a user's teeth and said toothbrush further having a tongue scraper disposed thereon.

7. A device according to claim 6, in which said elongated handle is integrally formed with said first and second flexible arms.

8. A device according to claim 6, in which said elongated handle further comprises first and second lateral protrusions.

9. A device according to claim 6, in which said elongated handle has an opening defined therein; whereby said opening is adapted to receive a hook therein to suspend said device from said hook.

10. A device according to claim 6, in which said toothbrush has first and second lateral bulges.

11. A device according to claim 6, in which said toothbrush is circular.

12. A device according to claim 6, in which said toothbrush is rectangular.

13. A device for oral hygiene comprising:

an elongated handle having first and second ends;

a gumbrush connected to said first end of said elongated handle, said gumbrush having first and second gumbrush heads, first and second flexible arms and first and second sets of bristles, each of said gumbrush heads having a respective one of said first and second sets of bristles disposed thereon; said first gumbrush head being attached to a first flexible arm, said first flexible arm being connected to said first end of said elongated handle, said second gumbrush head being attached to a second flexible arm, and said second flexible arm also being connected to said first end of said elongated handle;

whereby said first and second flexible arms are connected to said first end of said elongated handle so that said first and second heads are disposed in angled, generally opposing relationship to each other;

a toothbrush connected to said second end of said elongated handle, whereby said toothbrush is adapted to brush the crowns of a user's teeth, in which said elongated handle has a slot defined therein between first and second side walls of said handle whereby said slot is disposed adjacent said first end of said handle, and whereby said slot allows for inward flexure of said first and second side walls.

* * * * *